United States Patent [19]

Brenner et al.

[11] 4,118,567

[45] Oct. 3, 1978

[54] 3-MORPHOLINO-2-HETEROCYCLIC-THIO-PROPANAMIDES

[75] Inventors: L. Martin Brenner, Upper Darby; Bernard Loev, Broomall, both of Pa.

[73] Assignee: SmithKline Corporation, Philadelphia, Pa.

[21] Appl. No.: 265,941

[22] Filed: Jun. 23, 1972

[51] Int. Cl.$^2$ .............................................. C07D 413/06
[52] U.S. Cl. .................................... 544/131; 544/120; 544/122; 544/128; 544/133; 544/141; 424/248.5
[58] Field of Search ...................... 260/247.1, 294.8 E; 544/131

[56] References Cited

U.S. PATENT DOCUMENTS

| 2,953,562 | 9/1960 | Schuler et al. | 260/247.2 |
| 3,726,878 | 4/1973 | Kanai et al. | 260/294.8 E |
| 3,740,409 | 6/1973 | Brenner et al. | 260/294.8 E |

FOREIGN PATENT DOCUMENTS 2,100,970  3/1972  France.

Primary Examiner—Henry R. Jiles
Assistant Examiner—R. W. Ramsuer
Attorney, Agent, or Firm—Joan S. Keps; Richard D. Foggio; William H. Edgerton

[57] ABSTRACT

The compounds are 3-morpholino-2-heterocyclicthiopropanamides which are inhibitors of gastric acid secretion.

4 Claims, No Drawings

3-MORPHOLINO-2-HETEROCYCLIC-THIO-PROPANAMIDES

This invention relates to new 3-morpholino-2-heterocyclic-thiopropanamides having pharmacological activity. In particular, these compounds inhibit gastric acid secretion.

The compounds of this invention are represented by the following formula:

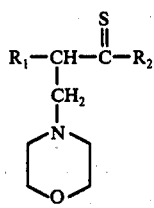

FORMULA I in which:
$R_1$ is 2-pyridyl, 2-pyrimidyl, 4-pyrimidyl, 2-pyrazinyl, 2-pyrrolyl, 2-quinolyl, 2-thiazolyl or 4-thiazolyl;
$R_2$ is

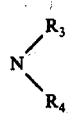

or NH—$(CH_2)_n$—cycloalkyl, said cycloalkyl having 3 to 6 carbon atoms;
$R_3$ and $R_4$ are hydrogen or lower alkyl and
$n$ is 0 or 1.

This invention also includes pharmaceutically acceptable acid addition salts of the compounds of Formula I.

The pharmacologically active compounds of this invention have the basic structure of Formula I. However, it is apparent to one skilled in the art that well known nuclear substituents such as lower alkyl, lower alkoxy or halogen may be incorporated on the heterocyclic rings of $R_1$. These substituted compounds are used as are the parent compounds.

Preferred compounds of this invention are represented by Formula I in which $R_2$ is $NH_2$, NH—(lower alkyl) or NH—$(CH_2)_n$—cycloalkyl, said cycloalkyl having 3-6 carbon atoms.

Most preferably, in the compounds of Formula I, $R_1$ is 2-pyridyl.

Particularly advantageous compounds of this invention are 3-morpholino-2-(2-pyridyl)thiopropanamide and N-methyl-3-morpholino-2-(2-pyridyl)thiopropanamide.

The compounds of this invention produce inhibition of gastric acid secretion. This activity is demonstrated by administration to pylorus ligated rats at doses of about 10 to about 50 mg./kg. orally. Also, this activity is demonstrated by administration to chronic gastric fistula rats (Brodie et al., *Amer. J. Physiol.* 202:812–814, 1962) at doses of about 50 mg./kg. orally. In these procedures, compounds which produce an increase in gastric juice pH or a decrease in the volume of gastric juice or both are considered active.

These compounds show antiulcer activity in the restraint-stress method in which on oral administration to rats these compounds inhibit the development of experimental ulcers.

3-Morpholino-2-(2-pyridyl)thiopropanamide, which is a compound of this invention, is a potent inhibitor of gastric acid secretion. On administration to pylorus ligated rats at 50 mg./kg. orally, this compound increased gastric juice pH by 5.8 units and decreased gastric juice volume by 4% (decreased titratable acid concentration by 98% and decreased titratable acid output by 99%) and at 10 mg./kg. it increased gastric juice pH by 1.8 units and decreased gastric juice volume by 57% (decreased titratable acid concentration by 79% and decreased titratable acid output by 92%). By contrast with the potency of this compound in increasing gastric juice pH, 2-morpholino-2-(2-pyridyl)thioacetamide, which is a compound known to the art (Belgian Pat. No. 770,592) has a low order of effect on gastric juice pH. The latter compound increased gastric juice pH by 0.73 units and decreased gastric juice volume by 58% on administration to pylorus ligated rats at 50 mg./kg. orally.

The compounds of this invention are prepared by the following procedures:

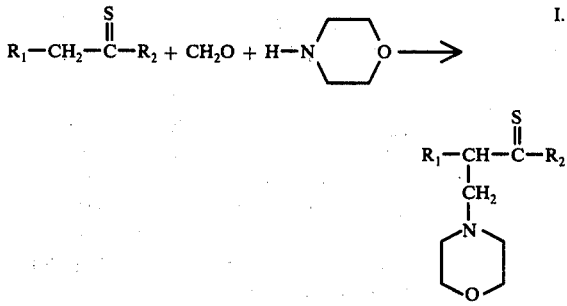

The terms $R_1$ and $R_2$ are as defined above.

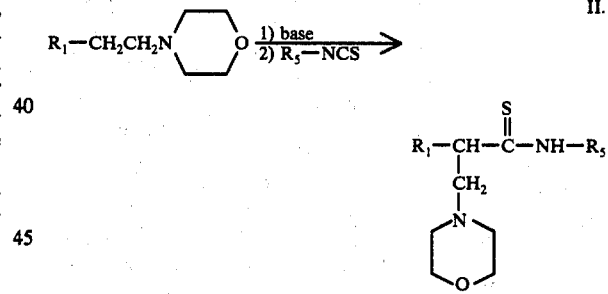

The term $R_1$ is as defined above and $R_5$ is lower alkyl or $(CH_2)_n$—cycloalkyl, said cycloalkyl having 3 to 6 carbon atoms and $n$ is as defined above.

According to procedure I, a 2-heterocyclic-thioacetamide is reacted with an equimolar amount of formaldehyde and an equimolar amount of morpholine.

According to procedure II, a 2-morpholinoethyl-heterocycle (which is prepared by reacting a vinyl-heterocycle or a 2-chloroethyl-heterocycle with morpholine) is reacted with strong base such as butyl or phenyl lithium and then with an appropriate isothiocyanate to give N-substituted 3-morpholino-2-heterocyclic-thiopropanamides of this invention.

Alternatively, the compounds of this invention are prepared by reacting a 2-heterocyclic-acetamide or a 2-heterocyclic-acetonitrile with an equimolar amount of formaldehyde and an equimolar amount of morpholine and when the resulting intermediate is a 3-morpholino-2-heterocyclic-propanamide, treating with phosphorus pentasulfide and when the resulting intermediate is a 3-morpholino-2-heterocyclic-propionitrile, reacting with hydrogen sulfide in the presence of a base such as an amine or by reacting with ammonium polysulfide.

The pharmaceutically acceptable, acid addition salts of the compounds of Formula I are formed with organic and inorganic acids by methods known to the art. For example, the base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, succinate, oxalate, benzoate, methanesulfonate, ethanedisulfonate, benzenesulfonate, acetate, propionate, tartrate, citrate, hydrochloride, hydrobromide, sulfate, sulfamate, phosphate and nitrate salts.

The compounds of this invention are administered internally either parenterally, rectally or, preferably, orally in an amount to produce the desired biological activity.

Preferably, the compounds are administered in conventional dosage forms prepared by combining an appropriate dose of the compound with standard pharmaceutical carriers.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200-400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The terms "lower alkyl" and "lower alkoxy" where used herein denote groups having 1–4 carbon atoms and "halogen" denotes chloro, bromo or fluoro.

The following examples are not limiting but are illustrative of the compounds of this invention and processes for their preparation.

EXAMPLE 1

A solution of 3.0 g. (0.019 mole) of 2-(2-pyridyl)thioacetamide in 40 ml. of anhydrous methanol is treated at −40° C. with 1.7 g. (0.019 mole) of morpholine in 5 ml. of methanol and 1.6 ml. of 37% formalin solution. The resulting mixture is kept at −25° C. for 36 hours.

The solvents are evaporated in vacuo at 25° C. and the residue is triturated three times with ether in the cold. The ether is decanted and the residue is recrystallized from acetone/hexane to give 3-morpholino-2-(2-pyridyl)thiopropanamide, m.p. 102°–104° C.

EXAMPLE 2

A solution of 1.0 g. (0.006 mole) of N-methyl-2-(2-pyridyl)thioacetamide in 20 ml. of methanol is treated with 0.78 g. (0.009 mole) of morpholine and 0.72 ml. of a 37% formalin solution. The resulting mixture is stirred at 25° C. for 48 hours. The solvent is removed in vacuo at 25° C. and the resulting oil is covered with petroleum ether. The oil slowly crystallizes and upon filtration and recrystallization from ethyl acetate, N-methyl-3-morpholino-2-(2-pyridyl)thiopropanamide, m.p. 116°–118° C., is obtained.

EXAMPLE 3

By the procedure of Example 2, the following thioacetamides are reacted with formaldehyde and morpholine:

N-methyl-2-(2-quinolyl)thioacetamide
N-ethyl-2-(6-methyl-2-pyridyl)thioacetamide
N-propyl-2-(6-methyl-2-pyridyl)thioacetamide
N-butyl-2-(6-methyl-2-pyridyl)thioacetamide
N,N-dimethyl-2-(2-pyridyl)thioacetamide
N,N-diethyl-2-(6-methyl-2-pyridyl)thioacetamide to give the following products, respectively:

N-methyl-3-morpholino-2-(2-quinolyl)thiopropanamide
N-ethyl-3-morpholino-2-(6-methyl-2-pyridyl)thiopropanamide
3-morpholino-N-propyl-2-(6-methyl-2-pyridyl)thiopropanamide
N-butyl-3-morpholino-2-(6-methyl-2-pyridyl)thiopropanamide
N,N-dimethyl-3-morpholino-2-(2-pyridyl)thiopropanamide
N,N-diethyl-3-morpholino-2-(6-methyl-2-pyridyl)thiopropanamide.

EXAMPLE 4

A solution of 7.6 g. (0.05 mole) of 2-(2-pyridyl)thioacetamide in a 40% aqueous solution of cyclopropylamine is refluxed for 45 minutes. After cooling, approximately 30 ml. of water is added. The reaction mixture is extracted three times with chloroform. The extracts are combined and dried over magnesium sulfate. The solvent is removed under reduced pressure. The residue is recrystallized twice from ethyl acetate/hexane to give N-cyclopropyl-2-(2-pyridyl)thioacetamide.

By the procedure of Example 2, N-cyclopropyl-2-(2-pyridyl)thioacetamide is reacted with formaldehyde and morpholine in methanol to give N-cyclopropyl-3-morpholino-2-(2-pyridyl)thiopropanamide.

Using in the above procedure the following cycloalkylamines:

cyclobutylamine
cyclopentylamine
cyclohexylamine the products are, respectively:

N-cyclobutyl-3-morpholino-2-(2-pyridyl)thiopropanamide
N-cyclopentyl-3-morpholino-2-(2-pyridyl)thiopropanamide
N-cyclohexyl-3-morpholino-2-(2-pyridyl)thiopropanamide.

EXAMPLE 5

Cyclopropanemethylamine hydrochloride (6.02 g., 0.056 mole) and 4.71 g. (0.056 mole) of sodium bicarbonate are dissolved in 75 ml. of water and the solution is added to 4.35 g. (0.029 mole) of 2-(2-pyridyl)thioacetamide. The reaction mixture is heated on a steam bath with stirring for four hours. The mixture is then cooled and 25 ml. of water is added. The reaction mixture is extracted three times with chloroform. The chloroform extracts are combined, dried over magnesium sulfate and then evaporated. The residue is purified by "dry-column" chromatography on silica gel, using ethyl acetate as solvent. The product is recrystallized from ethyl acetate/hexane to give N-cyclopropanemethyl-2-(2-pyridyl)thioacetamide.

By the procedure of Example 2, N-cyclopropanemethyl-2-(2-pyridyl)thioacetamide is reacted with formaldehyde and morpholine in methanol to give N-cyclopropanemethyl-3-morpholino-2-(2-pyridyl)thiopropanamide.

By the same procedure, using the following in place of cyclopropanemethylamine hydrochloride:

cyclobutanemethylamine hydrochloride
cyclopentanemethylamine hydrochloride
cyclohexanemethylamine hydrochloride the products are, respectively:

N-cyclobutanemethyl-3-morpholino-2-(2-pyridyl)thiopropanamide
N-cyclopentanemethyl-3-morpholino-2-(2-pyridyl)thiopropanamide
N-cyclohexanemethyl-3-morpholino-2-(2-pyridyl)thiopropanamide.

EXAMPLE 6

By the procedure of Example 1, using in place of 2-(2-pyridyl)thioacetamide, the following:

2-(2-quinolyl)thioacetamide
2-(2-pyrrolyl)thioacetamide
2-(2-pyrazinyl)thioacetamide the products are, respectively:

3-morpholino-2-(2-quinolyl)thiopropanamide
3-morpholino-2-(2-pyrrolyl)thiopropanamide
3-morpholino-2-(2-pyrazinyl)thiopropanamide.

EXAMPLE 7

A mixture of 7.2 g. of 2-pyrimidinemethanol and 25 ml. of thionyl chloride is heated for 4 hours on a steam bath, then concentrated under reduced pressure. The residue is dissolved in water and basified with 5% aqueous sodium bicarbonate solution. Extracting with ether, then drying and concentrating the extracts gives 2-(chloromethyl)pyrimidine.

A solution of 6.8 g. of 2-(chloromethyl)pyrimidine is added dropwise to a solution of 5.2 g. of sodium cyanide in 100 ml. of dimethylsulfoxide. The mixture is heated at 50° C. for 2 hours, then diluted with 150 ml. of 5% aqueous sodium carbonate solution and extracted with ether. The extract is dried and concentrated to give 2-(2-pyrimidyl)acetonitrile.

The above prepared 2-(2-pyrimidyl)acetonitrile is reacted with formaldehyde and morpholine in methanol to give 3-morpholino-2-(2-pyrimidyl)propionitrile.

Hydrogen sulfide is bubbled into a solution of 2.0 g. of 3-morpholino-2-(2-pyrimidyl)propionitrile in 100 ml. of dry pyridine containing 3.5 ml. of triethylamine for five hours. The solvent is removed under reduced pressure and chloroform is added to the residue. The mixture is allowed to stand at −20° C. overnight and then filtered to give 3-morpholino-2-(2-pyrimidyl)thiopropanamide.

EXAMPLE 8

Using 2-(chloromethyl)thiazole in the procedure of Example 7, the product is 3-morpholino-2-(2-thiazolyl)thiopropanamide.

EXAMPLE 9

In the procedure of Example 7, using 2-(4-thiazolyl)acetonitrile, the product is 3-morpholino-2-(4-thiazolyl)thiopropanamide.

EXAMPLE 10

4-Pyrimidinecarboxylic acid is reduced using lithium aluminum hydride in ether to give 4-pyrimidinemethanol.

Using 4-pyrimidinemethanol in the procedure of Example 7, the product is 3-morpholino-2-(4-pyrimidyl)thiopropanamide.

EXAMPLE 11

By the procedure of Example 4, using cyclopropylamine and the following thioacetamides:

2-(2-pyrazinyl)thioacetamide
2-(2-pyrrolyl)thioacetamide
2-(2-quinolyl)thioacetamide the products are, respectively:

N-cyclopropyl-3-morpholino-2-(2-pyrazinyl)thiopropanamide
N-cyclopropyl-3-morpholino-2-(2-pyrrolyl)thiopropanamide
N-cyclopropyl-3-morpholino-2-(2-quinolyl)thiopropanamide.

EXAMPLE 12

By the procedure of Example 5, using cyclopropanemethylamine hydrochloride and the following thioacetamides:

2-(2-pyrazinyl)thioacetamide
2-(2-pyrrolyl)thioacetamide
2-(2-quinolyl)thioacetamide the products are, respectively:

N-cyclopropanemethyl-3-morpholino-2-(2-pyrazinyl)thiopropanamide
N-cyclopropanemethyl-3-morpholino-2-(2-pyrrolyl)thiopropanamide
N-cyclopropanemethyl-3-morpholino-2-(2-quinolyl)thiopropanamide.

EXAMPLE 13

3Morpholino-2-(2-pyridyl)thiopropanamide (500 mg.) in ether is added to ethereal hydrogen chloride. The precipitate is filtered off and washed with ether to give 3-morpholino-2-(2-pyridyl)thiopropanamide dihydrochloride.

Similarly, using ethereal hydrogen bromide, the dihydrobromide salt is prepared.

EXAMPLE 14

N-Methyl-3-morpholino-2-(2-pyridyl)thiopropanamide in ethanol is treated with an equimolar amount of maleic acid in ethanol to give, after removing the solvent under reduced pressure, N-methyl-3-morpholino-2-(2-pyridyl)thiopropanamide maleate.

In the same manner, using citric acid, the citrate salt is prepared and using oxalic acid, the oxalate salt is prepared.

EXAMPLE 15

Alternatively, N-methyl-3-morpholino-2-(2-pyridyl)-thiopropanamide is prepared by the following procedure.

N-[2-(2-pyridyl)ethyl]morpholine (12.7 g., 0.07 mole) in 60 ml. of dry benzene is added dropwise to 35 ml. of 2M phenyl lithium (0.07 mole) in benzene/ether with cooling. The mixture is stirred for 30 minutes, then methyl isothiocyanate (5.2 g., 0.07 mole), dissolved in 60 ml. of dry benzene, is added dropwise with cooling. The resulting solution is stirred overnight. An equal volume of water is added and the solution is cooled and made acidic with 10% hydrochloric acid. The phases are separated, the organic phase is washed with water, and the combined aqueous phases are made basic to about pH 9, then extracted with chloroform. The chloroform extracts are washed with water and dried over magnesium sulfate. Filtration and removal of solvent gives a residue which is recrystallized from ethyl acetate to give N-methyl-3-morpholino-2-(2-pyridyl)thiopropanamide.

What is claimed is:

1. A compound of the formula:

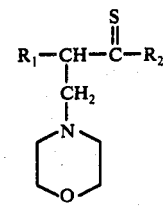

in which:
$R_1$ is 2-pyridyl;
$R_2$ is

or $NH-(CH_2)_n$—cycloalkyl, said cycloalkyl having 3 to 6 carbon atoms;
$R_3$ and $R_4$ are hydrogen or lower alkyl and
$n$ is 0 or 1
or a pharmaceutically acceptable acid addition salt thereof.

2. A compound of claim 1 in which $R_2$ is $NH_2$.
3. A compound of claim 1 in which $R_2$ is $NH_2$, NH—lower alkyl or $NH-(CH_2)_n$—cycloalkyl, said cycloalkyl having 3 to 6 carbon atoms and $n$ is 0 or 1.
4. A compound of claim 1 in which $R_2$ is $NH-CH_3$.

* * * * *